(12) United States Patent
Bradford et al.

(10) Patent No.: US 9,000,252 B2
(45) Date of Patent: Apr. 7, 2015

(54) WOUND DRESSING

(71) Applicant: Advanced Medical Solutions Limited, Winsford (GB)

(72) Inventors: Colin Bradford, Keighley (GB); Brian John Hamerslag, Higher Runcorn (GB)

(73) Assignee: Advanced Medical Solutions Limited, Winsford, Cheshire (GB)

( * ) Notice: Subject to any disclaimer, the term of this patent is extended or adjusted under 35 U.S.C. 154(b) by 224 days.

(21) Appl. No.: 13/886,756

(22) Filed: May 3, 2013

(65) Prior Publication Data

US 2013/0296818 A1 Nov. 7, 2013

(30) Foreign Application Priority Data

May 4, 2012 (GB) .................................. 1207852.3

(51) Int. Cl.
  *A61F 13/534* (2006.01)
  *A61F 13/00* (2006.01)
  *A61F 13/02* (2006.01)

(52) U.S. Cl.
  CPC ......... *A61F 13/00068* (2013.01); *Y10T 156/10* (2013.01); *A61F 13/00029* (2013.01); *A61F 13/022* (2013.01); *A61F 2013/00229* (2013.01); *A61F 2013/00744* (2013.01); *A61F 13/00987* (2013.01)

(58) Field of Classification Search
  CPC ............ A21F 13/00029; A21F 13/022; A21F 2013/00229; A21F 2013/00744
  USPC .......................................................... 604/368
  See application file for complete search history.

(56) References Cited

U.S. PATENT DOCUMENTS

| | | | | |
|---|---|---|---|---|
| 4,538,603 A | * | 9/1985 | Pawelchak et al. | 602/56 |
| 4,793,337 A | * | 12/1988 | Freeman et al. | 602/56 |
| 4,977,892 A | * | 12/1990 | Ewall | 602/52 |
| 5,219,325 A | * | 6/1993 | Hennink et al. | 602/41 |
| 2004/0049145 A1 | * | 3/2004 | Flick | 602/41 |
| 2005/0182347 A1 | * | 8/2005 | Bishop et al. | 602/43 |
| 2007/0255193 A1 | * | 11/2007 | Patel et al. | 602/48 |
| 2010/0030170 A1 | * | 2/2010 | Keller et al. | 604/360 |
| 2010/0030171 A1 | * | 2/2010 | Canada et al. | 604/360 |
| 2010/0030178 A1 | * | 2/2010 | MacMeccan et al. | 604/367 |
| 2011/0027344 A1 | * | 2/2011 | Lee et al. | 424/445 |
| 2011/0208145 A1 | * | 8/2011 | Zhang et al. | 604/368 |
| 2011/0213286 A1 | * | 9/2011 | Riesinger | 602/43 |
| 2013/0053748 A1 | * | 2/2013 | Cotton | 602/45 |
| 2013/0189339 A1 | * | 7/2013 | Vachon | 424/404 |
| 2014/0107555 A1 | * | 4/2014 | Patel | 602/48 |

FOREIGN PATENT DOCUMENTS

| | | |
|---|---|---|
| EP | 0 236 104 | 9/1987 |
| WO | WO 00/41661 | 7/2000 |
| WO | WO 2010/014171 | 2/2010 |

OTHER PUBLICATIONS

European Search Report dated Aug. 6, 2013 issued in connection with EP 13 27 5112.

* cited by examiner

*Primary Examiner* — Susan Su

(74) *Attorney, Agent, or Firm* — Nixon & Vanderhye P.C.

(57) ABSTRACT

A wound dressing comprises:
(i) a core of a non-woven layer comprising gelling fibres and having first and second major faces,
(ii) a first layer of an absorbent foam positioned with one face adjacent to the first face of the non-woven layer,
(iii) a second layer of an absorbent foam positioned with one face thereof adjacent to the second face of the non-woven layer,
(iv) an open material positioned against that face of the first absorbent foam layer remote from the non-woven layer; and
(v) an open material or a continuous semi-permeable film positioned against that face of the second absorbent layer remote from the non-woven layer.
Layers (i)-(v) may be bonded together.

23 Claims, No Drawings

WOUND DRESSING

This application claims priority to UK Application No.1207852.3 filed 4 May 2012, the entire contents of which is incorporated herein by reference.

The present invention relates to wound dressings for use particularly (but not necessarily exclusively) on moderate to heavily exuding wounds.

Absorbent wound dressings for moderate to heavily exuding wounds are typically constructed of either nonwoven materials (e.g. felt) or absorbent foams (e.g. polyurethane foams).

The nonwoven materials are usually produced from gelling fibres, i.e. fibres that form a gel when in contact with wound fluid (exudate) and largely lock this fluid within the structure of the material, thus providing the desirable attribute that the fluid is retained within the material and cannot be easily squeezed out. Examples of gelling fibres include alginate fibres, carboxymethylcellulose (CMC) fibres, carboxymethyl chitosan fibres, and other carboxymethylated/sulphonated fibres. Alternative gelling fibres are of superabsorbent materials such as polyacrylates (eg Oasis from Technical Absorbents Ltd), and these are generally blended with other fibres, usually non-gelling fibres such as viscose, polyester, acrylic, bicomponent fibres etc to form nonwoven materials. It is however possible for the superabsorbent fibres to be blended with gelling fibres as given above.

There are a range of medical grade polyurethane foams that are very absorbent and suitable for this use in wound dressings. Polyurethane foams used as wound dressings generally absorb more for the same area than felts for this use. This makes them very absorbent. However, they have a poor retention capability, and fluid can easily be squeezed out of them.

Both nonwovens and foams may incorporate antimicrobial agents and generally have the antimicrobial evenly distributed throughout the material. When such nonwovens or foams are in contact with wounds, there is the potential for the antimicrobial to elute out into the wound. However this elution must be controlled for a number of reasons. Firstly, for a product to be classed as a wound dressing, then its primary function must be either to manage exudate by absorption and/or transmission through the dressing, or in the case of hydrogels to hydrate necrotic and sloughy tissue. If elution is significant then the product may cease to be classed as a wound dressing with an ancillary (i.e. antimicrobial) action but rather needs to be classes as a drug delivery system. Secondly, it is desirable to keep the elution into the wound as low as possible as some antimicrobials, such as silver ions, can be cytotoxic.

It is an object of the invention to obviate or mitigate the above mentioned disadvantage.

According to the present invention there is provided a wound dressing comprising:

(i) a core of a non-woven layer comprising gelling fibres and having first and second major faces,
(ii) a first layer of an absorbent foam positioned with one face adjacent to the first face of the non-woven layer,
(iii) a second layer of an absorbent foam positioned with one face thereof adjacent to the second face of the non-woven layer,
(iv) an other open material positioned against that face of the first absorbent foam layer remote from the non-woven layer; and
(v) an open material or a continuous semi-permeable film positioned against that face of the second absorbent layer remote from the non-woven layer.

By "open material" we mean a material having openings for the direct passage of wound exudate therethrough. The open material used for layer (iv) and optionally also layer (v) may for example be an apertured film.

For the purposes of the following description, layer (iv) can be considered to be the wound-contacting layer of the dressing. It will however be noted that both layers (iv) and (v) may both be an open material (e.g. an apertured film), in which case the dressing may be applied to the wound either way up. However if layer (v) is a continuous semi-permeable film then the dressing can be considered to be "sided" and layer (iv) (i.e. the apertured film) will be applied to the wound. In this case, layer (v) (i.e. the continuous semi-permeable film) improves maintenance of a moist wound environment for improved healing, particularly in lower exuding wounds.

The combination of foam and a gelling nonwoven gives very good absorbency, but the retention of fluid is improved as the nonwoven retains fluid better than a foam. This improved retention of fluid (exudate) by the nonwoven layer provides the wound dressing of the invention with particular advantages in that the nonwoven layer may incorporate an antimicrobial agent and there is reduced potential for the antimicrobial to elute out of the dressing into the wound. In other words, the antimicrobial agent is retained within the nonwoven layer (and the potential for eluting from the dressing is reduced by the foam layers) and microorganisms are killed within the dressing.

Antimicrobial agents that may be used for the purposes of the invention may be any such agent which is suitable for use in a wound dressing. Non-limiting examples include compounds of metals such as silver, copper, or zinc, iodine based compounds, polyhexamethylene biguanide (PHMB) and derivatives, chlorohexidine gluconate/acetate, and Octenidine and derivatives.

The nonwoven layer is preferably in the form of a felt.

The gelling fibres of the nonwoven material may comprise superabsorbent fibres. In this case, the superabsorbent fibres will typically comprise 20 to 50% (more preferably 20 to 40%) by weight of the fibres of which the nonwoven material is comprised. The balance of the fibres may be provided by non-gelling fibres (present in this case in an amount of 50 to 80% by weight of the nonwoven material). Alternatively the balance of the fibres may be provided by other types of gelling fibres (i.e. non-superabsorbent) optionally together with non-gelling fibres.

In a further embodiment of the invention, the gelling fibres of the nonwoven material are comprised of gelling fibres which are otherwise than of the superabsorbent type. In this case, the nonwoven core is preferably comprised of at least 50%, more preferably at least 75%, even more preferably at least 90% and most preferably at least 95% by weight of such gelling fibres (i.e. of a type other than superabsorbent fibres). Such gelling fibres may be the only fibres in the nonwoven core. If however there are other fibre types in the nonwoven core then they will be of the non-gelling type.

Preferred examples of gelling fibres (which are other than of the superabsorbent type) for use in the invention include alginate fibres, carboxymethylcellulose (CMC) fibres, carboxymethyl chitosan fibres, and other carboxmethylated/sulphonated fibres.

The gelling fibres may be produced by standard techniques. Thus, for example, in the case of alginate fibres, these may be produced by spinning an aqueous dope comprising dissolved sodium alginate through a spinneret into a coagulating bath containing a multivalent cation, e.g. a divalent cation such as calcium, so as to produce an insoluble form of the alginate in the form of fibres in the coagulating bath.

Further details of a manufacturing process for producing alginate fibres are given in the Appendix.

Typically, the weight of the nonwoven material used for producing the core layer will be in the range of 70 to 400 g/m$^2$, more preferably 100 to 200 g/m$^2$. If the dressing is produced by a lamination process (see later), this is likely to compress the nonwoven layer, as it is less resilient than the foam, and hence reduce its absorbency. A higher weight is therefore required to allow for this compression to give the desired absorbency.

One or both of the layers of absorbent foam (i.e. layers (ii) and (iii)) may be comprised of an absorbent polyurethane foam. Generally the layers will be of the same foam material but this is not essential. Typically, each foam layer in the final dressing will have a thickness in the range of 1 to 6 mm, more preferably 1.5 to 3 mm. For the "non-sided" product where an apertured film is used on both sides, then the thickness of the foam layers will generally be the same. For the two sided product, then the thickness of each foam layer can be different.

Polyurethane foam for use in the invention may be produced by procedures that are entirely conventional in the art. Brief details of such processes are given in the Appendix.

In the wound dressing of the invention, the wound contact layer (iv) (which is considered to provide the wound contact layer) is in the form of an open material, e.g. an apertured film. Apertured films for use as layer (iv) can be of any suitable material for direct wound contact use, and one that has a low adherency, i.e. is unlikely to stick to wounds, such as polyurethane (PU), ethylmethyl methacrylate (EMA), Co-Polyester (CPET), polyethylene (PE), or silcone.

The apertured film should be such that the apertures are not too small to restrict the flow of exudate nor too large that sticking to the foam may occur. For circular apertures, the preferred size is 0.5-3.0 mm in diameter. Non-circular apertures of equivalent area may also be used. The preferred minimum dimension if the apertures are non-circular is 0.2 mm. The preferred open area of the film is 10-40%, more preferably 15-25%. If the wound contact material is an open material other than an apertured film, then it may for example be in the form of a net or an apertured nonwoven or woven material. The aperture sizes and open areas given above are also applicable to open materials other than films.

Apertured films as defined for use in layer (iv) are also suitable for use as layer (v).

In the case where a continuous semi-permeable film is used as layer (v) then it is preferable for the film to have a thickness of 15-75 μm, and that the overall moisture vapour transmission rate (MVTR) of the finished dressing should be in the range of 3,000-20,000 g/m$^2$/24 hr. Values less than 3000 are likely to cause skin maceration as they are not breathable enough, and values greater than 20,000 are likely to cause the wound to dry out and not maintain the moisture environment for optimal wound healing. Typically, the continuous semi-permeable film (if employed in the dressing) will be of a polyurethane. Conveniently, the film may be coloured so that the wound "contact side" and "non-contact side" may readily be distinguished.

In a preferred embodiment of the invention, the non-woven, core layer includes an antimicrobial agent. This has the advantage that when wound exudate is absorbed into the dressing, microorganisms in the exudate are killed not only within the non-woven material but also within the foam layers as a result of elution of the antimicrobial agent from the non-woven material into these layers. The foam layers will not necessary completely prevent transfer of the antimicrobial agent into the wound, but will restrict such transfer and hence make the dressing safer.

If an antimicrobial agent is to be included in the non-woven layer then it may be provided within the fibres themselves and/or on the surface thereof. The antimicrobial agent can be added in a number of ways. Thus, for example, when the fibres are prepared by spinning a dope into a coagulation bath, the antimicrobial agent may be included in the dope so that it becomes incorporated within the resulting fibres. In this way, the antimicrobial agent will be evenly distributed throughout each fibre. Alternatively, the antimicrobial agent may be incorporated into a liquid to be sprayed onto the fibres. This liquid may, for example, be a spin finish for the fibres or could be a liquid to be sprayed onto a tow of the fibres. In either case, the liquid is sprayed onto the fibres before cutting to final length. A further possibility is to apply the antimicrobial agent by dipping, coating or spraying a solution thereof onto a pre-formed felt.

It will be appreciated that any operation involving dipping, coating or spraying an aqueous solution of an antimicrobial agent onto the fibres (as a tow a pre-formed felt or otherwise) should not involve application of so much water than an undesired degree of gelling of the fibres occurs.

Layers (i)-(v) of the dressing should be bonded together so that the dressing remains integral and can easily be removed from the wound. It is particularly preferred that the bonds between (i) the non-woven layer core and (ii) the first layer of absorbent foam (i.e. between layers (a) and (b)) the non-woven layer core and the second layer of absorbent foam (i.e. layers (i) and (iii)) is provided by bonding the respective layers together by means of heat activated bonding webs. This ensures a strong bond, which is particularly desirable since the absorbent (e.g. polyurethane) foams can expand when wet and increase the stress on the bond. The use of heat activated bonding webs allows the dressing to remain integral.

Apertured films (as used for layer (iv) and possibly also layer (v)) and also continuous semi-permeable films (which may optionally be used for layer (v) can generally be bonded to the foam layers using heat alone.

In a typical method of producing the dressing in accordance with the invention, the layers (i)-(v) are assembled with heat activated bonding webs provided between (a) layers (i) and (ii), and between (b) layers (i) and (iii). The assembly may then be processed by conventional laminating apparatus so that the various layers are heat-bonded together. Polyurethane foams are particularly suitable as absorbent foam layers for dressings produced using a laminating process since they are resilient and generally loose little thickness and absorbency as a result of the lamination.

Although the use of heat activated bonding webs is a preferred method of producing wound dressings in accordance with the invention, it should be appreciated that the various layers may be bonded together by other techniques. Thus, for example, the layers may be bonded by adhesives which are activated either by heat or by pressure only. Alternatively, the construction of the layers may be such that they may be bonded together by heat only, without the need for adhesives or heat bonding webs.

The invention is illustrated by the following-limiting Example.

EXAMPLE 1

This Example illustrates production of one embodiment of wound dressing in accordance with the invention.

An assembly was prepared by placing the following 7 layers one on top of the other in the order indicated:

1) an apertured 15 μm polyurethane film (1.5 mm diameter holes, 20% open area);
2) 2 mm thick absorbent polyurethane foam (grade MCF.03 foam supplied by Advanced Medical Solutions B.V.);
3) heat activated bonding web (Ref M1590 supplied by Freudenberg);
4) Aquafiber alginate felt, 135 g/m² (supplied by Advanced Medical Solutions Limited);
5) heat activated bonding web (Ref M1590 supplied by Freudenberg);
6) 2 mm thick absorbent polyurethane foam (grade MCF.03 foam supplied by Advanced Medical Solutions B.V.); and
7) an apertured 15 μm polyurethane film (1.5 mm diameter holes, 20% open area).

The assembly of the above seven layers was bonded together by a single pass through a Reliant Powerbond laminater with both belts set to a temperature of 183° C., and with a tunnel gap of 5 mm and nip gap of 3.6 mm.

APPENDIX

1. Manufacturing Process For Alginate Fibres

Sodium alginate powder is water soluble and is mixed with water to form a thick liquid referred to as dope. Other ingredients can be added at this stage such as those that would improve absorbency or impart antimicrobial properties.

The additives can be in the form of powdered materials or liquids. Non-water soluble powders are mixed vigorously with the water prior to adding the sodium alginate, then continuously mixed until the dope has thickened up. This is to ensure the powders are evenly distributed.

For water soluble powders and liquids, the active levels in the finished fibres will need to be assessed to ensure they are not extracted in the subsequent processes.

The dope is pumped through a plate with lots of fine holes in to create individual filaments, into a bath containing calcium salts. An ion exchange reaction occurs where sodium is replaced with calcium to form water insoluble calcium alginate.

The filaments are washed, dried and cut into fibres.

2. Manufacturing Process For Needled Felts

Fibres are used for this process and generally have length within the range 30-75 mm. Virtually all fibres are crimped to assist with the processing, and frequently have a spin finish applied. The spin finish can impart various properties to the fibres such as wetting speed, hydrophobicity, change inter-fibre friction or reduce fibre breakages by acting as a lubricant.

Felts are manufactured in the following steps:
1 Opening—This is the first stage in separating clumps of fibres into individual fibres and is a coarse combing action. Fibres can be blended together at this stage.
2 Carding—This is a finer combing action to separate all the fibres and create a coherent, lightweight web. The fibres are largely orientated in the length direction (machine direction of the produced web).
3 Crosslapping—This lays down over lapping layers of the lightweight, carded web to build up the overall weight to the required level. This action turns the process flow through 90 degrees, and the fibres are now orientated across the width of the felt.
4 Needling—Numerous barbed needles penetrate the fibres, taking fibres from the surface into the middle, thereby entangling the fibres to create the felt. The needles only take fibres in one direction; the barbs of the needles have no effect on the way out. The quantity and type of needles, the speed of needling and the penetration depth control the felt properties. The needling action can be carried out in more than stage, and from one or both sides of the fibres.

The absorbent properties of the felt are dependent of the fibre type, weight of the felt and the degree of needling.

3. Manufacturing Process For Polyurethane Foams

Foams use a pre-polymer of polyurethane, which is reactive with water. The pre-polymer is mixed with water that usually includes a surfactant. This physical mixing along with the reaction with the water causes foaming. The foam is extruded onto a conveyor to form a sheet or block where foaming continues for a short period of time.

The sheets or blocks are dried to remove the water, and cut to the desired thickness.

The invention claimed is:

1. A wound dressing comprising:
   (i) a core of a non-woven layer comprising gelling fibres and having first and second major faces,
   (ii) a first layer of an absorbent foam positioned with one face adjacent to the first face of the non-woven layer,
   (iii) a second layer of an absorbent foam positioned with one face thereof adjacent to the second face of the non-woven layer,
   (iv) an open material positioned against that face of the first absorbent foam layer remote from the non-woven layer; and
   (v) an open material or a continuous semi-permeable film positioned against that face of the second absorbent layer remote from the non-woven layer.

2. A dressing as claim 1 where the non-woven core layer is produced from alginate or predominately alginate fibres.

3. A dressing as in claim 1 where the absorbent foam is polyurethane.

4. A dressing as claimed in claim 1 wherein the open material for use as layer (iv) or (v) has apertures with an area equivalent to circular apertures having a diameter of 0.5 to 3.0 mm in diameter.

5. A dressing as claimed in claim 1 wherein the open material of layer (iv) or (v) has a open area of 10 to 40%.

6. A dressing as claimed in claim 5 wherein the open material of layer (iv) or (v) has a open area of 10 to 25%.

7. A dressing as claimed in claim 1 wherein layer (iv) and/or (v) is an apertured film.

8. A dressing as in claim 7 wherein layer (iv) is a polyurethane (PU), ethylmethyl methacrylate (EMA), Co-Polyester (CPET), or polyethylene (PE) or silicone apertured film.

9. A dressing as claimed in claim 1 wherein layer (v) is a polyurethane (PU), ethylmethyl methacrylate (EMA), Co-Polyester (CPET), polyethylene (PE).

10. A dressing as in claimed in claim 1 wherein layer (v) is a continuous semi-permeable polyurethane film.

11. A dressing as claimed in claim 1 where the absorbent foam layers are 1 to 6 mm in thickness.

12. A dressing as claimed in claim 1 wherein the non-woven layer comprises 20 to 50% of superabsorbent fibres, the balance of the fibres being non-gelling fibres and/or gelling fibres of other than a superabsorbent material.

13. A dressing as claimed in claim 1 wherein the non-woven layer comprises at least 50% by weight of gelling fibres other than of a superabsorbent material.

14. A dressing as claimed in claim 13 wherein said gelling fibres are alginate fibres.

15. A dressing as claimed in claim 1 wherein the non-woven core layer has weight in the range 70 to 400 g/m².

16. A dressing as claimed in claim 1 wherein layers (i)-(v) are bonded together.

17. A dressing as claimed in claim 16 wherein the foam layers (ii) and (iii) are bonded to the non-woven core layer (i) by heat activated bonding webs.

18. A dressing as claimed in claim 1 wherein the non-woven core layer contains an antimicrobial agent.

19. A dressing as claimed in claim 18 wherein the antimicrobial is a compound of metals such as silver, copper or zinc, iodine based compounds, polyhexamethylene biguanide (PHMB) and derivatives or chlorohexidine gluconate/acetate or octenidine and derivatives.

20. A method of preparing a wound dressing comprising the steps of:
(a) preparing an assembly comprised of
   (i) a core of a non-woven layer comprising gelling fibres and having first and second major faces,
   (ii) a first layer of an absorbent foam positioned with one face adjacent to the first face of the non-woven layer,
   (iii) a second layer of an absorbent foam positioned with one face thereof adjacent to the second face of the non-woven layer,
   (iv) an apertured film or other open material positioned against that face of the first absorbent foam layer remote from the non-woven layer; and
   (v) an apertured film or a continuous semi-permeable film positioned against that face of the second absorbent layer remote from the non-woven layer; and
(b) bonding layers (i)-(v) together.

21. A method as claimed in claim 20 wherein layer (i) contains an antimicrobial agent.

22. A method as claimed in claim 20 wherein step (b) is affected with heat.

23. A method as claimed in claim 22 wherein heat activated bonding layers are interposed between layers (i) and (ii) and between layers (i) and (iii).

* * * * *